(12) United States Patent
Tian et al.

(10) Patent No.: US 7,734,437 B2
(45) Date of Patent: *Jun. 8, 2010

(54) APPARATUS FOR DESIGNING AN OPTICAL METROLOGY SYSTEM OPTIMIZED WITH SIGNAL CRITERIA

(75) Inventors: Xinkang Tian, San Jose, CA (US); Manuel Madriaga, San Jose, CA (US); Ching-Ling Meng, Sunnyvale, CA (US); Mihail Mihalov, San Jose, CA (US)

(73) Assignee: Tokyo Electron Limited, Tokyo (JP)

( * ) Notice: Subject to any disclaimer, the term of this patent is extended or adjusted under 35 U.S.C. 154(b) by 74 days.

This patent is subject to a terminal disclaimer.

(21) Appl. No.: 12/057,332

(22) Filed: Mar. 27, 2008

(65) Prior Publication Data

US 2009/0248340 A1    Oct. 1, 2009

(51) Int. Cl.
*G06F 19/00* (2006.01)
*G01B 11/14* (2006.01)

(52) U.S. Cl. ............... 702/82; 700/121; 356/625
(58) Field of Classification Search ............... 702/81, 702/82; 356/600, 601, 625; 438/7, 16; 700/121
See application file for complete search history.

(56) References Cited

U.S. PATENT DOCUMENTS

| 7,589,845 B1 * | 9/2009 | Tian et al. ............... 356/625 |
| 2006/0064280 A1 * | 3/2006 | Vuong et al. ............... 702/182 |
| 2008/0106729 A1 * | 5/2008 | Vuong et al. ............... 356/73 |

* cited by examiner

*Primary Examiner*—Bryan Bui
(74) *Attorney, Agent, or Firm*—Manuel B. Madriaga

(57) ABSTRACT

Provided is an apparatus for designing an optical metrology system for measuring structures on a workpiece wherein the optical metrology system is configured to meet one or more signal criteria. The design of the optical metrology system is optimized by using collected signal data in comparison to set one or more signal criteria. In one embodiment, the optical metrology system is used for stand alone systems. In another embodiment, the optical metrology system is integrated with a fabrication cluster in semiconductor manufacturing.

20 Claims, 9 Drawing Sheets

APPARATUS FOR DESIGNING AN OPTICAL METROLOGY SYSTEM OPTIMIZED WITH SIGNAL CRITERIA

BACKGROUND

1. Field

The present application generally relates to the design of an optical metrology system to measure a structure formed on a workpiece, and, more particularly, to a system to optimize the design of an optical metrology system to meet one or more signal criteria.

2. Related Art

Optical metrology involves directing an incident beam at a structure on a workpiece, measuring the resulting diffraction signal, and analyzing the measured diffraction signal to determine various characteristics of the structure. The workpiece can be a wafer, a substrate, photomask or a magnetic medium. In manufacturing of the workpieces, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured diffraction signal) is compared to a library of simulated diffraction signals. Each simulated diffraction signal in the library is associated with a hypothetical profile. When a match is made between the measured diffraction signal and one of the simulated diffraction signals in the library, the hypothetical profile associated with the simulated diffraction signal is presumed to represent the actual profile of the periodic grating. The hypothetical profiles, which are used to generate the simulated diffraction signals, are generated based on a profile model that characterizes the structure to be examined. Thus, in order to accurately determine the profile of the structure using optical metrology, a profile model that accurately characterizes the structure should be used.

With increased requirement for throughput, decreasing size of the test structures, smaller spot sizes, and lower cost of ownership, there is greater need to optimize design of optical metrology systems to meet one or more signal criteria. Characteristics of the signal such as signal intensity, signal-to-noise ratio, and repeatability of diffraction signal measurements are essential to meeting the increased requirement for throughput, smaller spot size, and lower cost of ownership of the optical metrology system.

SUMMARY

Provided is an apparatus for designing an optical metrology system for measuring structures on a workpiece wherein the optical metrology system is configured to meet one or more signal criteria. The design of the optical metrology system is optimized by using collected signal data in comparison to set one or more signal criteria. In one embodiment, the optical metrology system is used for standalone systems. In another embodiment, the optical metrology system is integrated with a fabrication cluster in semiconductor manufacturing.

BRIEF DESCRIPTION OF DRAWINGS

FIG. 7A is an exemplary diagram of a detector subsystem that includes a photodiode array whereas

DETAILED DESCRIPTION

In order to facilitate the description of the present invention, a semiconductor wafer may be utilized to illustrate an application of the concept. The systems and processes equally apply to other workpieces that have repeating structures. The workpiece may be a wafer, a substrate, disk, or the like. Furthermore, in this application, the term structure when it is not qualified refers to a patterned structure.

Figure 1A:
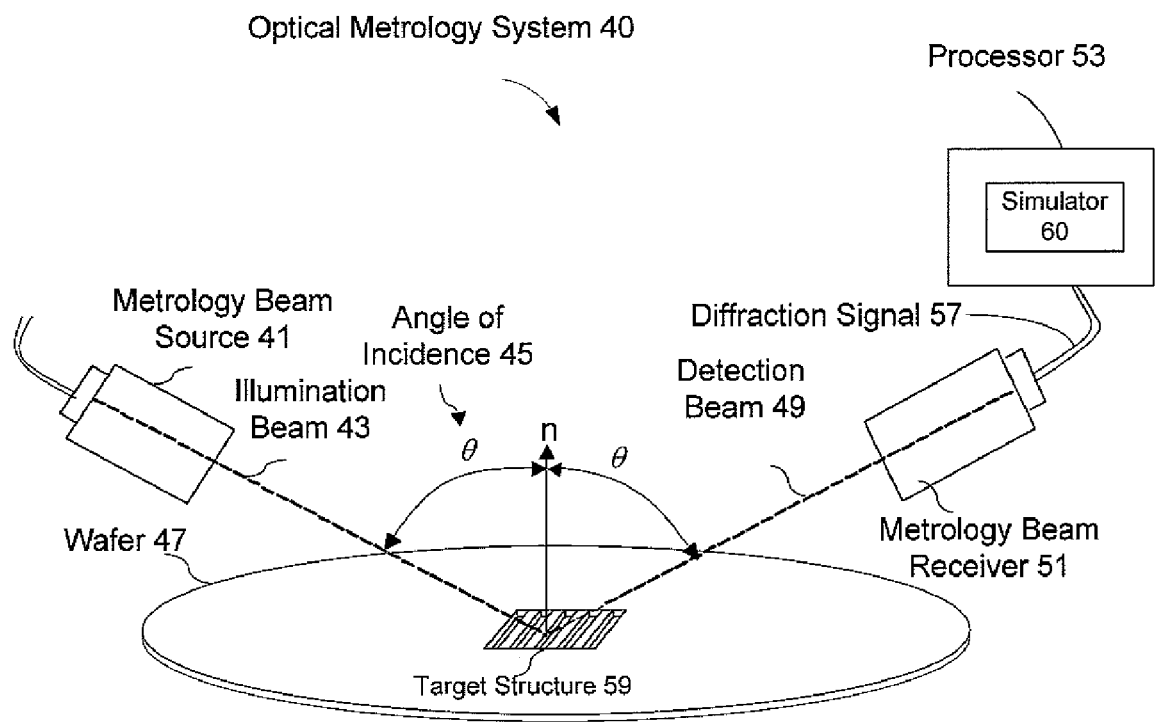
FIG. 1A is an architectural diagram illustrating an exemplary embodiment where an optical metrology system can be utilized to determine the profiles of structures formed on a semiconductor wafer.

FIG. 1A is an architectural diagram illustrating an exemplary embodiment where optical metrology can be utilized to determine the profiles or shapes of structures fabricated on a semiconductor wafer. The optical metrology system 40 includes a metrology beam source 41 projecting a metrology illumination beam 43 at the target structure 59 of a wafer 47. The metrology beam 43 is projected at an incidence angle θ towards the target structure 59. The diffracted detection beam 49 is measured by a metrology beam receiver 51. A measured diffraction signal 57 is transmitted to a processor 53. The processor 53 compares the measured diffraction signal 57 against a simulator 60 of simulated diffraction signals and associated hypothetical profiles representing varying combinations of critical dimensions of the target structure and resolution. The simulator can be either a library that consists of a machine learning system, pre-generated data base and the like (this is library system), or on demand diffraction signal generator that solves the Maxwell equation for a giving profile (this is regression system). In one exemplary embodiment, the diffraction signal generated by the simulator 60 instance best matching the measured diffraction signal 57 is selected. The hypothetical profile and associated critical dimensions of the selected simulator 60 instance are assumed to correspond to the actual cross-sectional shape and critical dimensions of the features of the target structure 59. The optical metrology system 40 may utilize a reflectometer, an ellipsometer, or other optical metrology device to measure the diffraction beam or signal. An optical metrology system is described in U.S. Pat. No. 6,913,900, entitled GENERATION OF A LIBRARY OF PERIODIC GRATING DIFFRACTION SIGNAL, issued on Sep. 13, 2005, which is incorporated herein by reference in its entirety.

Simulated diffraction signals can be generated by applying Maxwell's equations and using a numerical analysis technique to solve Maxwell's equations. It should be noted that various numerical analysis techniques, including variations of rigorous coupled wave analysis (RCWA), can be used. For a more detail description of RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety.

Simulated diffraction signals can also be generated using a machine learning system (MLS). Prior to generating the simulated diffraction signals, the MLS is trained using known input and output data. In one exemplary embodiment, simulated diffraction signals can be generated using an MLS employing a machine learning algorithm, such as back-propagation, radial basis function, support vector, kernel regression, and the like. For a more detailed description of machine learning systems and algorithms, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Figure 1B:
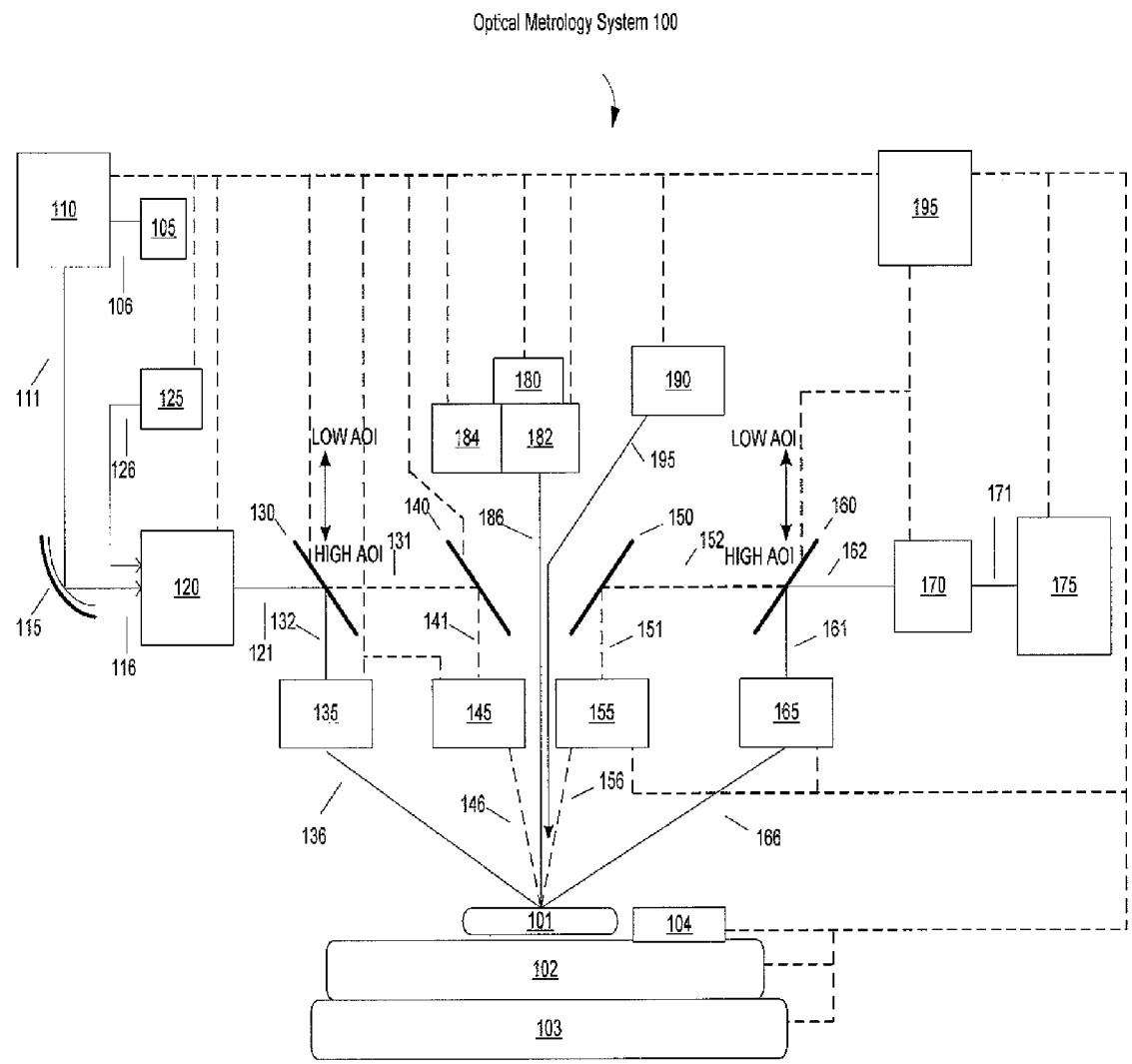
FIG. 1B depicts an exemplary optical metrology system in accordance with embodiments of the invention.

FIG. 1B shows an exemplary block diagram of an optical metrology system in accordance with embodiments of the invention. In the illustrated embodiment, an optical metrology system 100 can comprise a lamp subsystem 105, coupled to an illuminator subsystem 110. At least two optical outputs 111 from the illuminator subsystem 110 can be transmitted to a selector subsystem 115. The selector subsystem 115 can send at least two signals 116 to a beam generator subsystem 120. In addition, a reference subsystem 125 can be used to provide at least two reference outputs 126 to the beam generator subsystem 120. The wafer 101 is positioned using an X-Y-Z-theta stage 102 where the wafer 101 is adjacent to a wafer alignment sensor 104, supported by a platform base 103.

The optical metrology system 100 can comprise a first selectable reflection subsystem 130 that can be used to direct at least two outputs 121 from the beam generator subsystem 120 on a first path 131 when operating in a first mode "LOW AOI" or on a second path 132 when operating in a second mode "HIGH AOI". When the first selectable reflection subsystem 130 is operating in the first mode "LOW AOI", at least two of the outputs 121 from the beam generator subsystem 120 can be directed to a first reflection subsystem 140 as outputs 131, and at least two outputs 141 from the first reflection subsystem can be directed to a high angle focusing subsystem 145. When the first selectable reflection subsystem 130 is operating in the second mode "HIGH AOI", at least two of the outputs 121 from the beam generator subsystem 120 can be directed to a low angle focusing subsystem 135 as outputs 132. Alternatively, other modes in addition to "LOW AOI" and "HIGH AOI" may be used and other configurations may be used.

When the metrology system 100 is operating in the first mode "LOW AOI", at least two of the outputs 146 from the high angle focusing subsystem 145 can be directed to the wafer 101. For example, a high angle of incidence can be used. When the metrology system 100 is operating in the second mode "HIGH AOI", at least two of the outputs 136 from the low angle focusing subsystem 135 can be directed to the wafer 101. For example, a low angle of incidence can be used. Alternatively, other modes may be used and other configurations may be used.

The optical metrology system 100 can comprise a high angle collection subsystem 155, a low angle collection subsystem 165, a second reflection subsystem 150, and a second selectable reflection subsystem 160.

When the metrology system 100 is operating in the first mode "LOW AOI", at least two of the outputs 156 from the wafer 101 can be directed to the high angle collection subsystem 155. For example, a high angle of incidence can be used. In addition, the high angle collection subsystem 155 can process the outputs 156 obtained from the wafer 101 and high angle collection subsystem 155 can provide outputs 151 to the second reflection subsystem 150, and the second reflection subsystem 150 can provide outputs 152 to the second selectable reflection subsystem 160. When the second selectable reflection subsystem 160 is operating in the first mode "LOW AOI" the outputs 152 from the second reflection subsystem 150 can be directed to the analyzer subsystem 170. For example, at least two blocking elements can be moved allowing the outputs 152 from the second reflection subsystem 150 to pass through the second selectable reflection subsystem 160 with a minimum amount of loss.

When the metrology system 100 is operating in the second mode "HIGH AOI", at least two of the outputs 166 from the wafer 101 can be directed to the low angle collection subsystem 165. For example, a low angle of incidence can be used. In addition, the low angle collection subsystem 165 can process the outputs 166 obtained from the wafer 101 and low angle collection subsystem 165 can provide outputs 161 to the second selectable reflection subsystem 160. When the second selectable reflection subsystem 160 is operating in the second mode "HIGH AOI" the outputs 162 from the second selectable reflection subsystem 160 can be directed to the analyzer subsystem 170.

When the metrology system 100 is operating in the first mode "LOW AOI", high incident angle data from the wafer 101 can be analyzed using the analyzer subsystem 170, and when the metrology system 100 is operating in the second mode "HIGH AOI", low incident angle data from the wafer 101 can be analyzed using the analyzer subsystem 170.

Metrology system 100 can include at least two measurement subsystems 175. At least two of the measurement subsystems 175 can include at least two detectors such as spectrometers. For example, the spectrometers can operate from the Deep-Ultra-Violet to the visible regions of the spectrum.

The metrology system 100 can include at least two camera subsystems 180, at least two illumination and imaging subsystems 182 coupled to at least two of the camera subsystems 180. In addition, the metrology system 100 can also include at least two illuminator subsystems 184 that can be coupled to at least two of the imaging subsystems 182.

In some embodiments, the metrology system 100 can include at least two auto-focusing subsystems 190. Alternatively, other focusing techniques may be used.

At least two of the controllers (not shown) in at least two of the subsystems (105, 110, 115, 120, 125, 130, 135, 140, 145, 150, 155, 160, 165, 170, 175, 180, 182 and 190) can be used when performing measurements of the structures. A controller can receive real-signal data to update subsystem, processing element, process, recipe, profile, image, pattern, and/or model data. At least two of the subsystems (105, 110, 115, 120, 125, 130, 135, 140, 145, 150, 155, 160, 165, 170, 175, 180, 182 and 190) can exchange data using at least two Semiconductor Equipment Communications Standard (SECS) messages, can read and/or remove information, can feed forward, and/or can feedback the information, and/or can send information as a SECS message.

Those skilled in the art will recognize that at least two of the subsystems (105, 110, 115, 120, 125, 130, 135, 140, 145, 150, 155, 160, 165, 170, 175, 180, 182 and 190) can include computers and memory components (not shown) as required. For example, the memory components (not shown) can be used for storing information and instructions to be executed by computers (not shown) and may be used for storing temporary variables or other intermediate information during the execution of instructions by the various computers/processors in the metrology system 100. At least two of the subsystems (105, 110, 115, 120, 125, 130, 135, 140, 145, 150, 155, 160, 165, 170, 175, 180, 185 and 190) can include the means for reading data and/or instructions from a computer readable medium and can comprise the means for writing data and/or instructions to a computer readable medium. The metrology system 100 can perform a portion of or all of the processing steps of the invention in response to the computers/processors in the processing system executing at least two sequences of at least two instructions contained in a memory and/or received in a message. Such instructions may be received from another computer, a computer readable medium, or a network connection. In addition, at least two of the subsystems (105, 110, 115, 120, 125, 130, 135, 140, 145, 150, 155, 160, 165, 170, 175, 180, 182 and 190) can comprise control applications, Graphical User Interface (GUI) components, and/or database components.

It should be noted that the beam when the metrology system 100 is operating in the first mode "LOW AOI" with a high incident angle data from the wafer 101 all the way to the measurement subsystems 175, (output 166, 161, 162, and 171) and when the metrology system 100 is operating in the second mode "HIGH AOI" with a low incident angle data from the wafer 101 all the way to the measurement subsystems 175, (output 156, 151, 152, 162, and 171) is referred to as diffraction signal(s).

Figure 2:
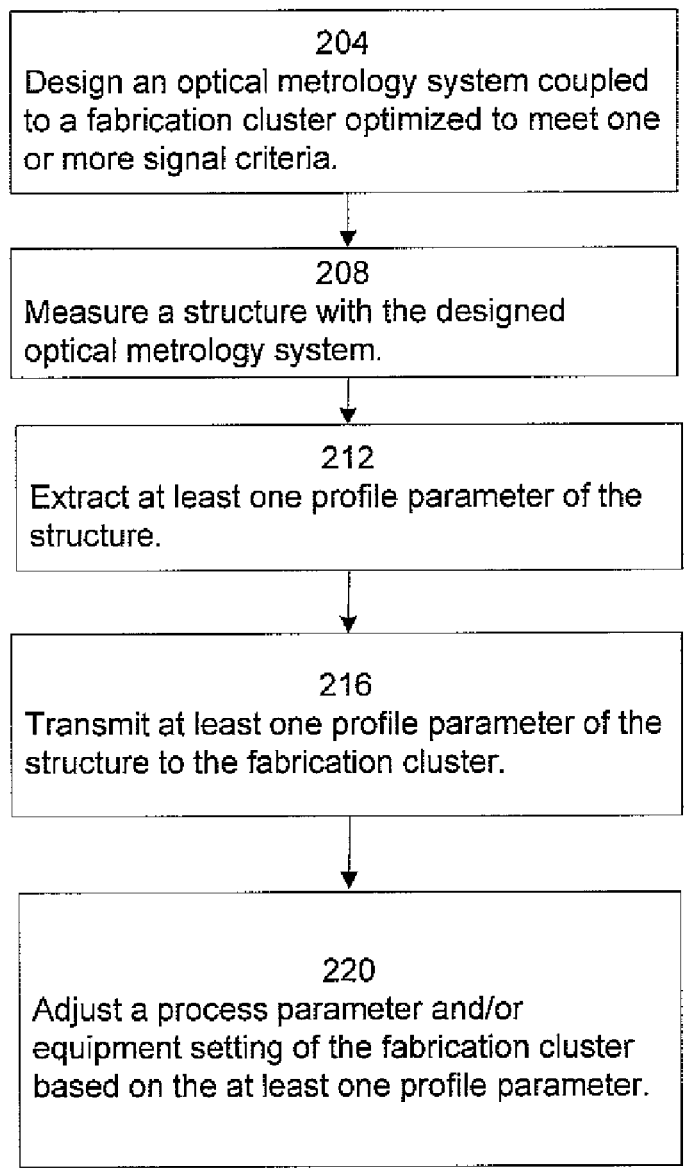
FIG. 2 depicts an exemplary flowchart for designing a metrology system for extracting structure profile parameters and controlling a fabrication process.

FIG. 2 depicts an exemplary flowchart for designing an optical metrology system for extracting structure profile parameters and controlling a fabrication process for semiconductors. In this exemplary embodiment, the optical metrology system is integrated in a semiconductor fabrication cluster. In step 204, an optical metrology system coupled to a semiconductor fabrication cluster is designed to meet one or more signal criteria. The fabrication cluster may be a lithography, etch, cleaning, chemical-mechanical polishing fabrication cluster, deposition cluster, or the like. The optical metrology system includes an optical metrology tool such as a spectroscopic reflectometer, spectroscopic ellipsometer, hybrid optical device, and the like. The detail steps for designing the optical metrology system are included in the description associated with the flowchart in FIG. 4.

Still referring to FIG. 2, in step 208, a structure is measured with the designed optical metrology system generating a diffraction signal. As mentioned above, the workpiece may be a wafer, a substrate, disk, photomask or the like. In step 212, at least one profile parameter of the structure is extracted from the measured diffraction signal using the systems and systems such as regression system, the library system or machine learning systems system described above. In step 216, at least one profile parameter of the structure extracted is transmitted to the fabrication cluster. Extracted profile parameters may include critical dimensions such as bottom width, top width or sidewall angle of the structure. In step 220, at least one process parameter or equipment setting of the fabrication cluster is adjusted based on the transmitted profile parameters.

Figure 3:
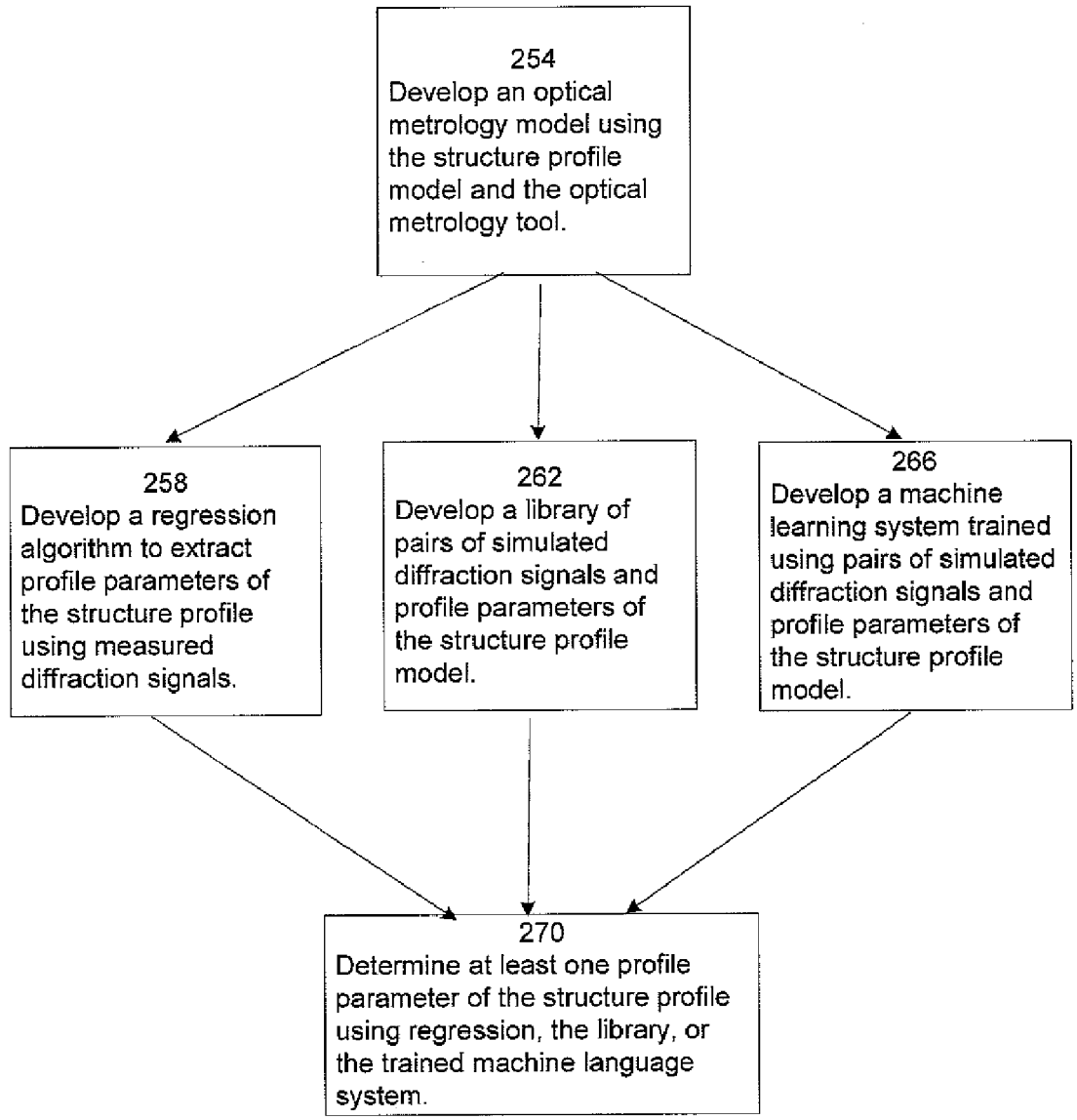
FIG. 3 depicts an exemplary flowchart for a system for extracting structure profile parameters using measurements from the optical metrology system.

FIG. 3 depicts an exemplary flowchart for a system for extracting structure profile parameters using measurements from the optical metrology system. In step 254, an optical metrology model is developed using the profile model of the structure and the designed optical metrology system. As mentioned above, the profile of the structure may be a simple line and space grating or a more complex group of repeating structures such as posts, contact holes, vias, or combinations of different shapes structures in a repeating pattern of unit cells. For a detailed description of modeling two-dimensional repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated in its entirety herein by reference. The optical metrology model includes characterization of the illumination beam that is used to illuminate the structure and characterization of the detection beam diffracted from the structure.

In step 258, a regression algorithm is developed to extract the profile parameters of the structure profile using measured diffraction signals. Typically, the regression algorithm compares a series of simulated diffraction signals generated from a set of profile parameters where the simulated diffraction signal is matched to the measured diffraction signal until the matching criteria are met. For a more detailed description of a regression-based process, see U.S. Pat. No. 6,785,638, titled SYSTEM AND SYSTEM FOR DYNAMIC LEARNING THROUGH A REGRESSION-BASED LIBRARY GENERATION PROCESS, filed on Aug. 6, 2001, which is incorporated herein by reference in its entirety.

In step 262, a library of pairs of simulated diffraction signals and profile parameters of the structure are generated. For a more detailed description of an exemplary library-based process, see U.S. Pat. No. 6,943,900, titled GENERATION OF A LIBRARY OF PERIODIC GRATING DIFFRACTION SIGNALS, issued on Sep. 13, 2005, which is incorporated herein by reference in its entirety. In step 266, an MLS is trained using pairs of simulated diffraction signals and profile parameters. The trained MLS is configured to generate a set of profile parameters as output based on an input measured diffraction signal. For a more detailed description of a generating and using a trained MLS, see U.S. Pat. No. 7,280, 229, titled EXAMINING A STRUCTURE FORMED ON A SEMICONDUCTOR WAFER USING MACHINE LEARNING SYSTEMS, filed on Dec. 3, 2004, which is incorporated herein by reference in its entirety. In step 270, at least one profile parameter of the structure profile is determined using the regression algorithm, the library, the trained MLS. It should be noted that the steps described above, (254, 258, 262, 264, 268, and 270), apply to an optical metrology system in a fabrication cluster or to a standalone optical metrology system.

Figure 4:
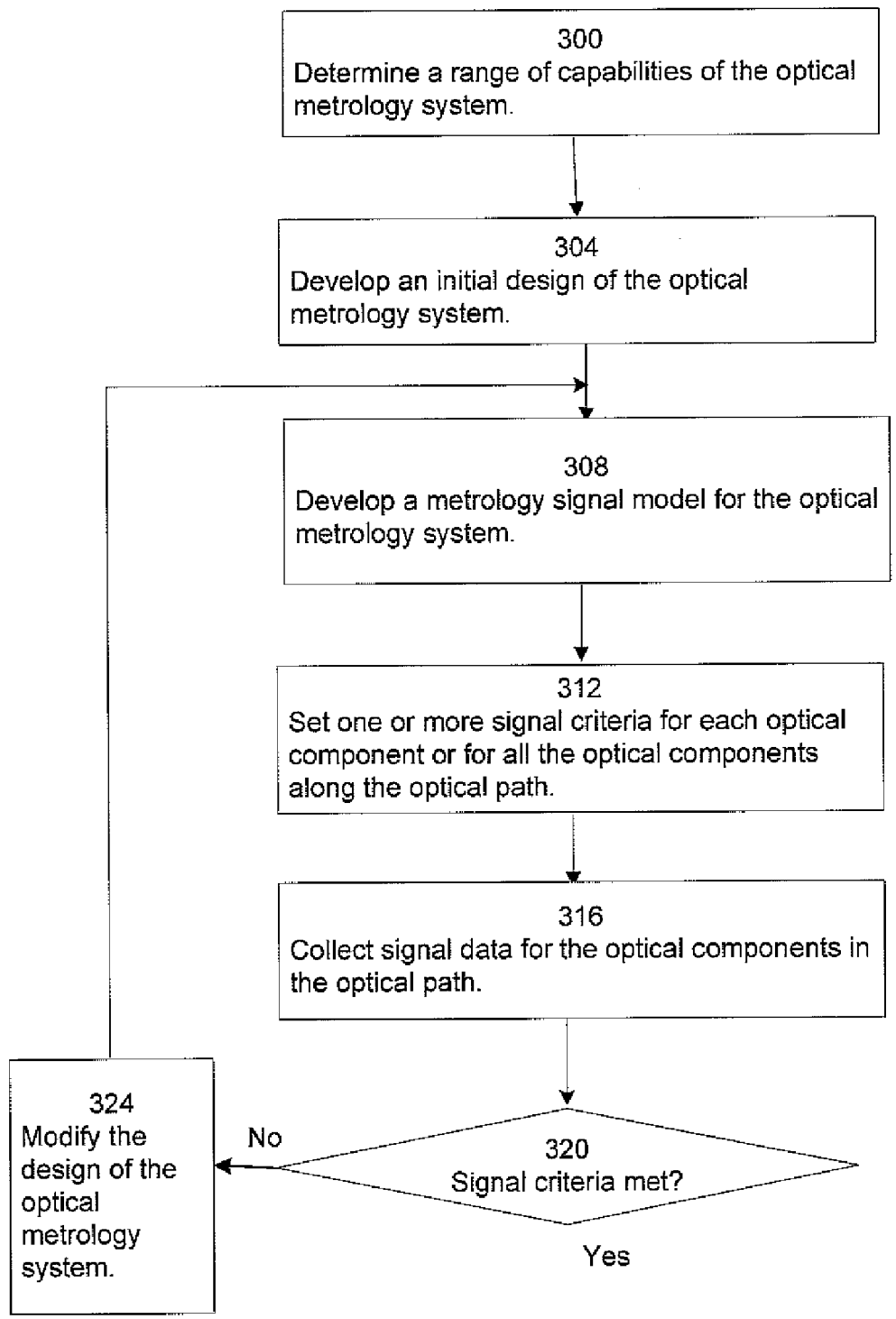
FIG. 4 depicts an exemplary flowchart for optimizing the design of an optical metrology system based on one or more signal criteria.

FIG. 4 depicts an exemplary flowchart for optimizing the design of an optical metrology system based on achieving one or more signal criteria. In step 300, the range of capabilities of the optical metrology system is determined. The range of capabilities of the optical metrology system may include the types of wafer applications that can be measured which in turn determines the number of measurement beams and optical paths, the range of illumination angle of incidence, number of measurement sites per wafer, the number of measurements per site, and the like. For example, if an optical metrology system is designed to measure one-dimensional repeating structures comprising lines and spaces, two measurement beams may be specified and the illumination beam of incidence would more likely use a fixed angle of incidence. If an optical metrology system is designed to measure both one-dimensional repeating structures and complex two-dimensional repeating structures, two or more measurement beams with a range of illumination beam angles of incidence may be specified. In step 304, an initial design of the optical metrology system is developed based on the range of capabilities determined in the step 300. The initial design includes components of the optical metrology system comprising light sources, homogenizer to produce a uniform light spot, focusing optics for the illumination beams and coating specification for the focusing optics, polarizers for the illumination beams and detection beams, collecting optics for the detection beams, at least two detectors for measuring the diffraction signals and efficiency of the detector gratings, use of a nitrogen-purged system, a first processor for converting the measured diffraction output to diffraction data, data storage for storing profile parameter extraction algorithms, libraries, or trained machine learning systems, and a second processor for extracting at least one parameter of the structure from the diffraction signal. Furthermore, the measured diffraction signal may be processed to increase the signal to noise ratio by using the first processor and algorithms for minimizing systematic noise from the signal. For details on minimizing systematic noise from the signal, refer to U.S. application Ser. No. 12/018028 titled "NOISE REDUCTION METROLOGY MODELS", by Li, et al., filed on Jan. 22, 2008, which is incorporated herein by reference in its entirety.

In step 308, a metrology signal model for the optical metrology system is developed. Components of the metrology signal model comprise optical components that modify or alter the characteristics of the output signal from the device compared to the input signal into the device, namely, the optical component changes the intensity and/or phase of the signal, the signal-to-noise ratio (SNR), or other characteristics of the signal such as repeatability of the measurement. The optical components include the light sources that output the signal at an intensity based on the light source type and specifications, a beam homogenizer type and specifications, the focusing optics type and coating specifications, the type and specifications of the polarizer on the illumination side, the type and specifications of the polarizer on the detection side, (also known as analyzer), the focusing optics type and coating specifications on the detection side, efficiency of the detector gratings, the type and specifications of the spectrometer, use of a nitrogen-purged system, and other optical components such as flip-in mirrors, collimating mirrors and the like. The metrology signal model can include the input signal intensity to an optical component and an algorithm or a function that determines the output signal intensity from the optical component. In other embodiments, the metrology signal model includes selected optical components along the optical path or all the optical components along the optical path that modify or alter the characteristics of the signal, from the light source to the spectrometer.

For example, an element of the metrology signal model may include an input signal intensity of 100 joules to an illumination polarizer, an algorithm or function that determines the output signal, and the output signal coming out at 37 to 40 joules based on the type and specifications of the polarizer. As mentioned above, in one embodiment, the metrology signal model includes the output signal intensity from the light source, a set of algorithms or functions that determine the output signal intensity for all the optical components along the optical path, and the final signal intensity output onto the spectrometer. For example, the output signal intensity from the light source may be 100 joules and the final signal intensity output onto the spectrometer may be 2 joules after processing using the algorithms or functions for the optical components along the optical path.

Referring to FIG. 4, in step 312, one or more signal criteria for each optical component that modify or alter the characteristics of the input signal into device compared to the output signal from the device are set. Based on the initial design of the optical metrology system developed in step 304, the type and specifications of the optical components are determined. For example, if the initial design called for an illumination angle of incidence of about 65 degrees from normal and use of reflective optics to focus the illumination beam, the optical components that would modify the signal includes the mirror for deflecting the beam from the illumination polarizer and the set of focusing mirrors. The one or more signal criteria are set for the mirror to deflect the beam from the illumination polarizer and also for each of the focusing mirrors. In one embodiment, the one or more criteria can be set from the light source to the last optical component of the optical metrology system or prior to the spectrometer. As an example, if the light source starts with 100 joules, the one or more signal criteria may include the signal intensity input into the spectrometer. As mentioned above, the one or more signal criteria may include the signal intensity expressed in watts per second or joules, the signal-to-noise ratio expressed as a number with noise as 1, for example, a signal to noise ratio of 2000, and/or repeatability of the signal measurements expressed as standard deviation from the mean, and the like. In other embodiments, the signal intensity may be expressed as optical energy according the formula:

$$\text{Optical energy} = \text{Intensity} \times \text{Collection Area} \times \text{Integration Time} \quad (1.1.0)$$

where Intensity is expressed in watts/area, area is measured in square meters or square centimeters, Collection Area is measured in square meters or square centimeters, and Integration Time is measured in seconds. In still another embodiment, the one or more signal criteria may include percentage efficiency of conversion of the input signal into optical component. For example, the signal intensity criterion set for illumination focusing optics may be an efficiency of conversion of input signal intensity to output signal intensity of 80% or better.

In step 316, the signal data for each optical component or the signal data at the end of a group of optical components are collected. The signal data collected corresponds to the one or more signal criteria set in step 312, such as signal intensity or signal-to-noise ratio, and the like. Signal data for the optical components may be collected using a breadboard model of the optical metrology system or by using the vendor specifications for components specified for the optical metrology system. In step 320, the output signal collected for each optical component and/or the signal collected at the end of the optical path are compared to their respective signal criterion. If the one or more signal criteria are not met after each optical component or if the one or more signal criteria are not met after a group of optical components or at the end of the optical path, in step 324, the design of the optical metrology system is modified and steps 308, 312, 316, 320, and 324 are iterated until the one or more signal criteria are met. In another embodiment, only the one or more signal criteria at the end of the optical path or prior to the spectrometer are set. The signal data at the end of the optical path or prior to the spectrometer are collected and compared to the overall one or more signal criteria. If the signal criteria are not met, in step 324, the design of the optical metrology system is modified and steps 308, 312, 316, 320, and 324 are iterated until the one or more signal criteria are met.

Modification of the design of the of the optical metrology system can include selecting two or more light sources utilizing different ranges of wavelengths instead of utilizing one light source, illuminating the structure at substantially the same spot with the two or more beams from the two or more light sources at the same time, measuring the two or more diffraction signals off the structure and using a separate detector for each of the two or more diffraction signals instead of one detector; selecting an off-axis reflectometer wherein the angle of incidence of the illumination beam is substantially around 28 degrees instead of a normal or near normal angle of incidence; selecting an off-axis reflectometer wherein the angle of incidence of the illumination beam is substantially around 65 degrees instead of a near normal reflectometer or instead of 28 degrees; or reducing the number of optical components needed to implement the design. In other embodiments, modification of the design of the of the optical metrology system can include selecting a first polarizer in the illumination path and a second polarizer (or analyzer) in the detection path, wherein the first and second polarizers are configured to increase the signal to noise ratio of the illumination and detection beams respectively instead of regular polarizers or substituting the first polarizer and the second polarizer with polarizers from another vendor, replacing mirrors and focusing optics with different quality coatings, replacement of diffractive optic with reflective optics, and the like.

Still referring to step 324, modification of the design of the of the optical metrology system can also include using a selectable angle of incidence for the illumination beam to optimize accuracy of the diffraction measurement instead of a fixed angle of incidence of the illumination beams; different design of the slits for beam control, higher efficiency grating and higher efficiency signal detector, configurable numerical aperture for the focusing optics, light source, and the like. It is understood that any change in the design of the optical metrology system that can reduce the loss of signal intensity or increase the signal to noise ratio in the output signal, increase repeatability of signal measurement can be included in the list of design changes for step 324.

Figure 5:
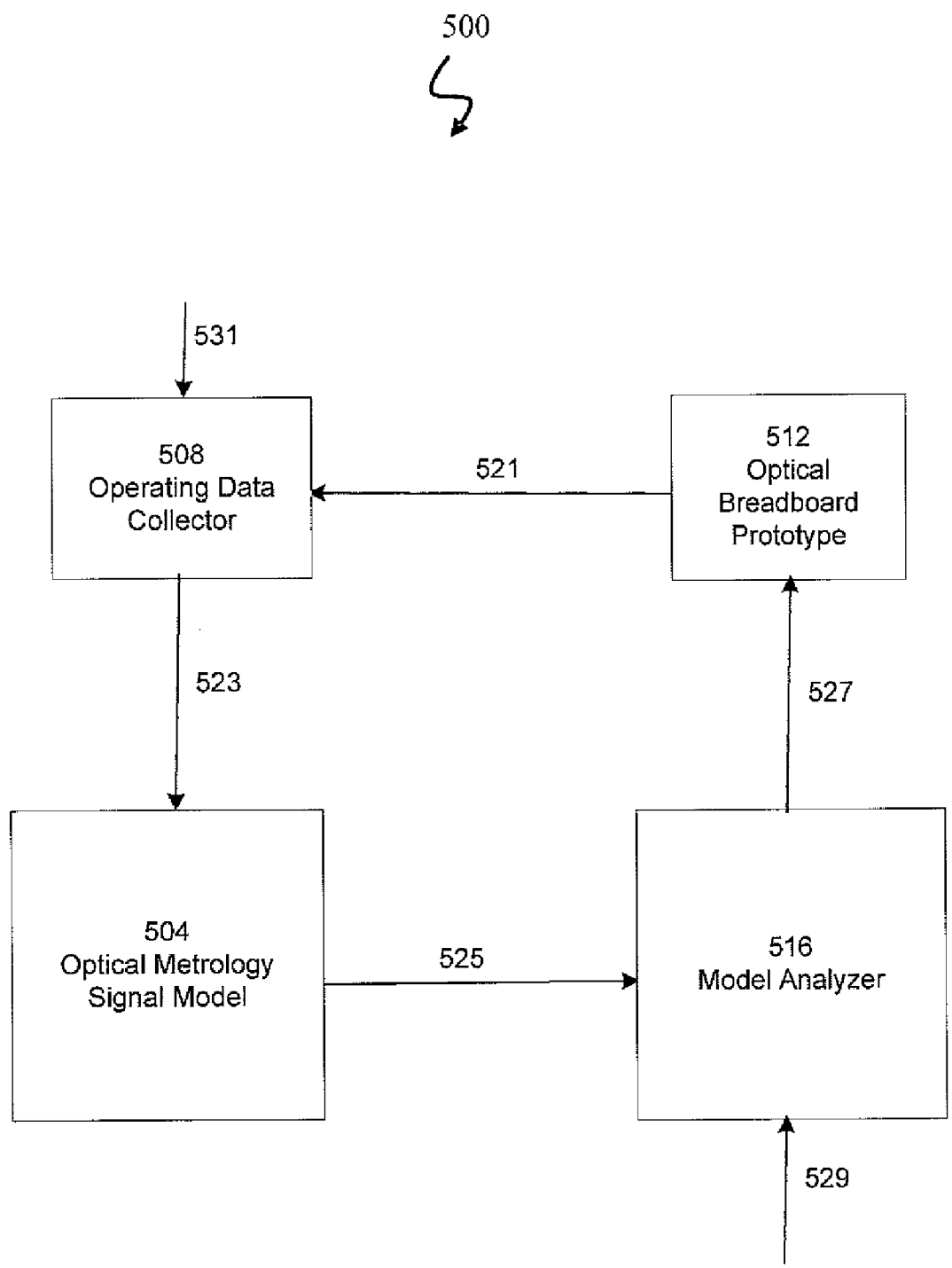
FIG. 5 is an exemplary block diagram of a system to optimize the design of an optical metrology system using one or more signal criteria.

FIG. 5 is an exemplary block diagram of a system 500 to optimize the design of the optical metrology system to meet one or more signal criteria. The system 500 comprises an optical metrology signal model 504, an operating data collector 508, an optical breadboard prototype 512, and a model analyzer 516 are coupled to collect and optimize the signal performance of a particular design of the optical metrology system. The optical metrology signal model 504 includes optical components of the optical metrology system that modify or alter the characteristics of the output signal from the component compared to the input signal. Included in the optical metrology signal model 504 are algorithms or functions for calculating the output signal from the input signal, using data about the optical components based on model, vendor and controllable variables available with the specific optical components. For example, the optical component such as the illuminator or the focusing optics may have a configurable numerical aperture (NA) that can be varied based on the vendor specifications and depending on the NA configured for an application, the output signal from the optical component may be different. The optical breadboard prototype 512 comprises optical metrology system components that are coupled to simulate the performance of the actual optical metrology system. In an optical breadboard prototype for an optical metrology system, as many of the actual optical components are utilized to test out the optical path and connections between mechanical and electronic components. For example, the optical breadboard prototype may include a motion control subsystem (not shown) programmed to position the wafer to the selected measurement sites, focusing subsystems in the illumination and detection optical paths, and a pattern recognition subsystem (not shown) to determine the orientation of the wafer, where the pattern recognition subsystem is coupled to the motion control subsystem.

Referring to FIG. 5, the signal data 521 such as signal intensity or SNR from the light source measured in the optical breadboard prototype 512 is transmitted to the operating data collector 508. In addition, signal data from the vendors or historical signal data 531 for similar optical components are input into the operating data collector 508, where the collections of signal data 523 for the different optical components from the operating data collector 508 are further sent to the optical metrology signal model 504. The collections of signal data 523 is processed by the optical metrology signal model 504 to generate the signal data for each optical component or for a group of optical components, and/or generate the signal data 525 for last optical component in the optical path and transmit the signal data 525 to the model analyzer 516. The model analyzer 516 compares the calculated one or more signal criteria of the optical components, or for a group of optical components, and/or the last signal criteria 525 for all the optical components with the corresponding set one or more signal criteria. Based the results of the comparison in the model analyzer 516, modifications to the optical metrology system design 527 are determined and transmitted to and/or implemented in the optical breadboard prototype 512.

As mentioned above, modification of the design of the of the optical metrology system can include selecting two or more light sources utilizing different ranges of wavelengths instead of utilizing two light sources with a similar range of wavelengths, illuminating the structure at substantially the same spot with the two or more beams from the two or more light sources at the same time, measuring the two or more diffraction signals off the structure and using a separate detector for each of the two or more diffraction signals instead of one light source; selecting an off-axis reflectometer wherein the angle of incidence of the illumination beam is substantially around 28 degrees instead of a normal or near normal angle of incidence; selecting an off-axis reflectometer wherein the angle of incidence of the illumination beam is substantially around 65 degrees instead of a near normal reflectometer instead of 28 degrees; or reducing the number of optical components needed to implement the design. In other embodiments, modification of the design of the of the optical metrology system can include selecting a first polarizer in the illumination path and a second polarizer (or analyzer) in the detection path, wherein the first and second polarizers are configured to increase the signal to noise ratio of the illumination and detection beams respectively instead of regular polarizers or substituting the first polarizer and the second polarizer with polarizers from another vendor, replacing mirrors and focusing optics with different quality coatings, replacement of diffractive optic with reflective optics, and the like. Additional modification of the design of the of the optical metrology system can also include using a selectable angle of incidence for the illumination beam to optimize accuracy of the diffraction measurement instead of a fixed angle of incidence of the illumination beams; different design of the slits for beam control, higher efficiency grating and signal detector, configurable numerical aperture for the focusing optics, light source, and the like.

The changes to the design of the optical breadboard prototype 512 are also incorporated in the operating data collector 508 and into the optical metrology signal model 504. A new set of signal measurements 521 from the optical breadboard prototype 512 and from vendor data 531 are input into the operating data collector 508 and transmitted to the optical metrology signal model 504, generating new signal data to compare to the set one or more signal criteria. Changes to the design of the optical breadboard prototype 512, updates to the operating data collector 508 and to the optical metrology signal model 504, and the series of processing in the model analyzer 516 are iterated until the one or more signal criteria are met.

Figure 6:
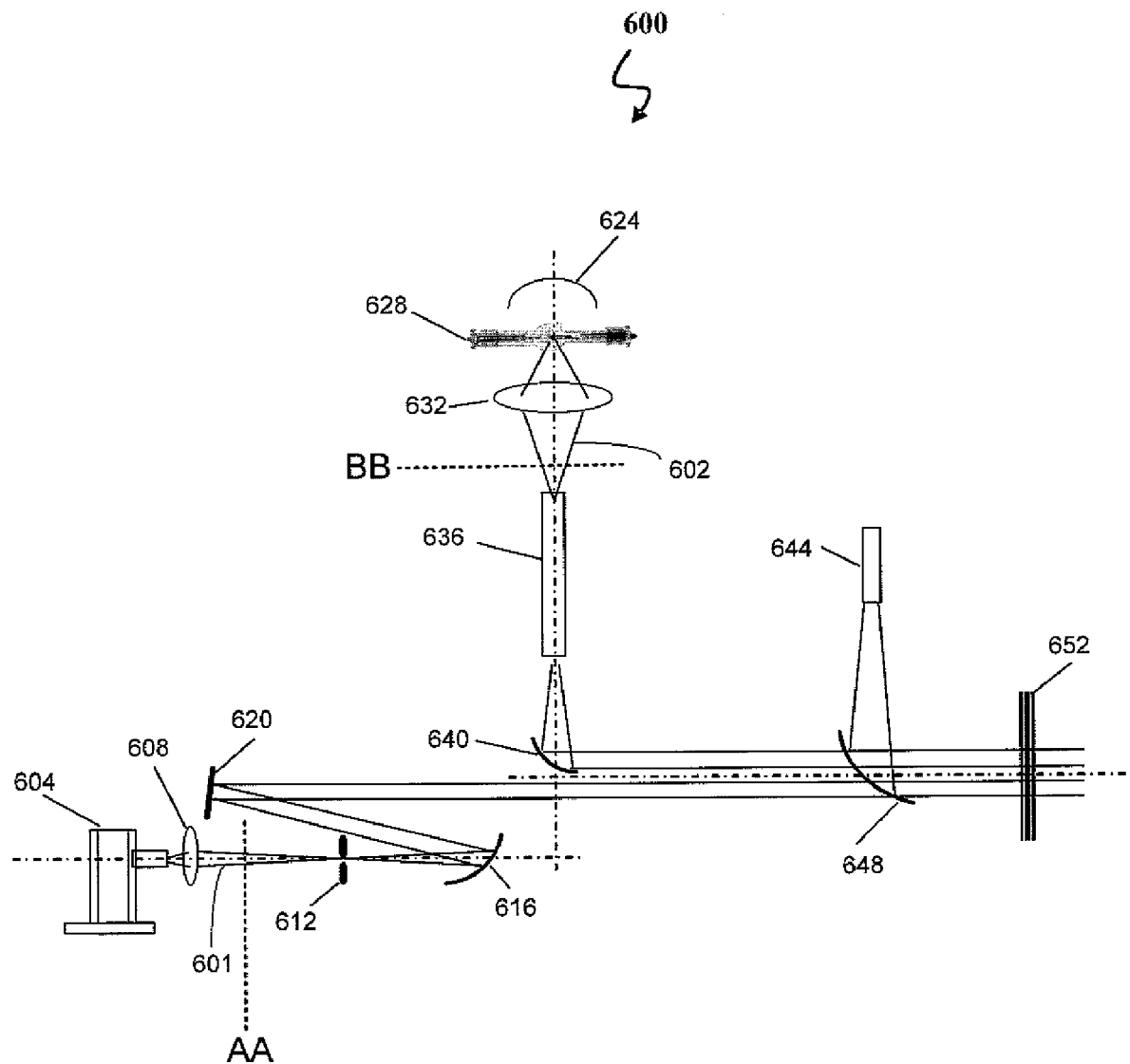
FIG. 6 is an exemplary diagram of a dual light source subsystem comprising a deuterium lamp and a xenon lamp light sources in an embodiment of the invention.

FIG. 6 is an exemplary diagram of a dual light source subsystem 600 comprising a deuterium lamp 604 and a xenon lamp 628 light sources in an embodiment of the invention. The deuterium lamp 604 emits an illumination beam through a condenser lens 608 and a spatial filter 612 onto a parabolic mirror 616. The deuterium illumination beam 601 reflected by the parabolic mirror 616 is directed to the mirror 620 through shutter 652 and on to the remainder of the optical path (not shown). Illumination from the xenon lamp 628 is reflected by the spherical reflector 624 through a condenser lens 632 into a homogenizer 636. The xenon illumination beam 602 is directed by parabolic mirror 640 through the shutter 652 and on to the remainder of the optical path (not shown). Light from a spectral lamp 644 is also directed by a parabolic mirror 648 onto the remainder of the optical path (not shown). Other illumination beams may be used in addition to deuterium illumination beam 601 and xenon illumination beam 602. As mentioned above, two or more illumination beams with different ranges wavelengths may be used. Measurements conducted on the optical breadboard prototype 512 in FIG. 5 can be done by inserting a photodetector (not shown) at any stage along the optical path of the deuterium illumination beam 601 at position AA for example and for the xenon illumination beam 602 at position BB in FIG. 6.

Figure 7A:
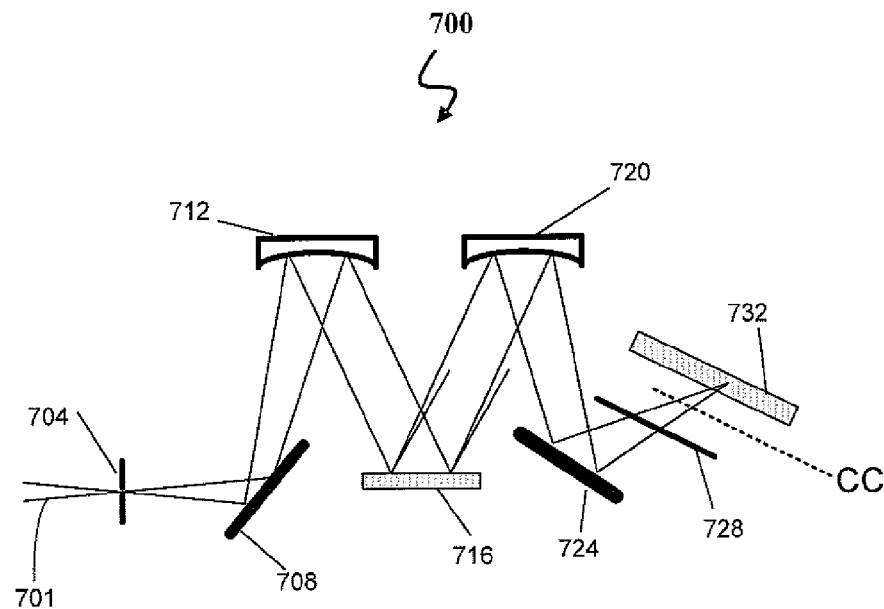

FIG. 7A is an exemplary diagram of a detector subsystem 700 that includes a photodiode array. The detection beam 701 passes through a pinhole 704 and is reflected by a mirror 708 onto a collimating mirror 712 which reflects the collimated beam to a grating 716 that separates the detection beam into separate wavelengths onto a focusing mirror 720, proceeds onto another mirror 724, passes through a filter 728 and is directed to the photodiode array 732 where the beam data is measured as signal intensity. Measurements conducted on the optical breadboard prototype 512 in FIG. 5 can be done by inserting a photodetector (not shown) at any stage along the optical path of illumination beam 701 in FIG. 7A, for example at position CC.

Figure 7B:
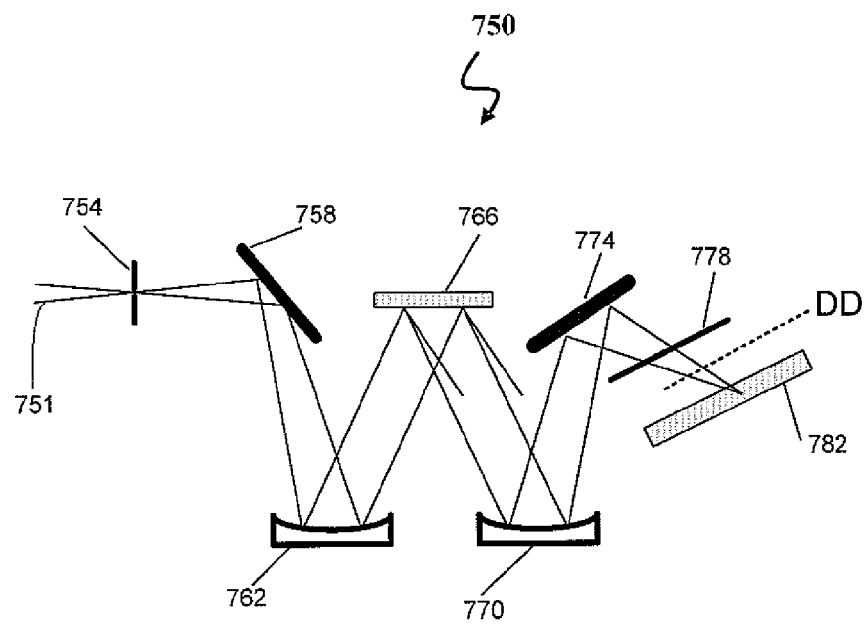
FIG. 7B is an exemplary diagram of a detector subsystem that includes a charge coupled device (CCD) array.

FIG. 7B is an exemplary diagram of a detector subsystem 750 that includes a charge coupled device (CCD) array. The detection beam 751 passes through a pinhole 754 and is reflected by a mirror 758 onto a collimating mirror 762 which reflects the collimated beam to a grating 766 that separates the detection beam into separate wavelengths onto a focusing mirror 770, proceeds onto another mirror 774, passes through a filter 778 and is directed to the CCD array 782 where the beam data is measured as signal intensity. Measurements conducted on the optical breadboard prototype 512 in FIG. 5 can be done by inserting a photodetector (not shown) at any stage along the optical path of illumination beam 751, for example, in position DD in FIG. 7B. As mentioned above, two or more detection beams with different ranges wavelengths measured each by a detector array may be used.

Figure 8:
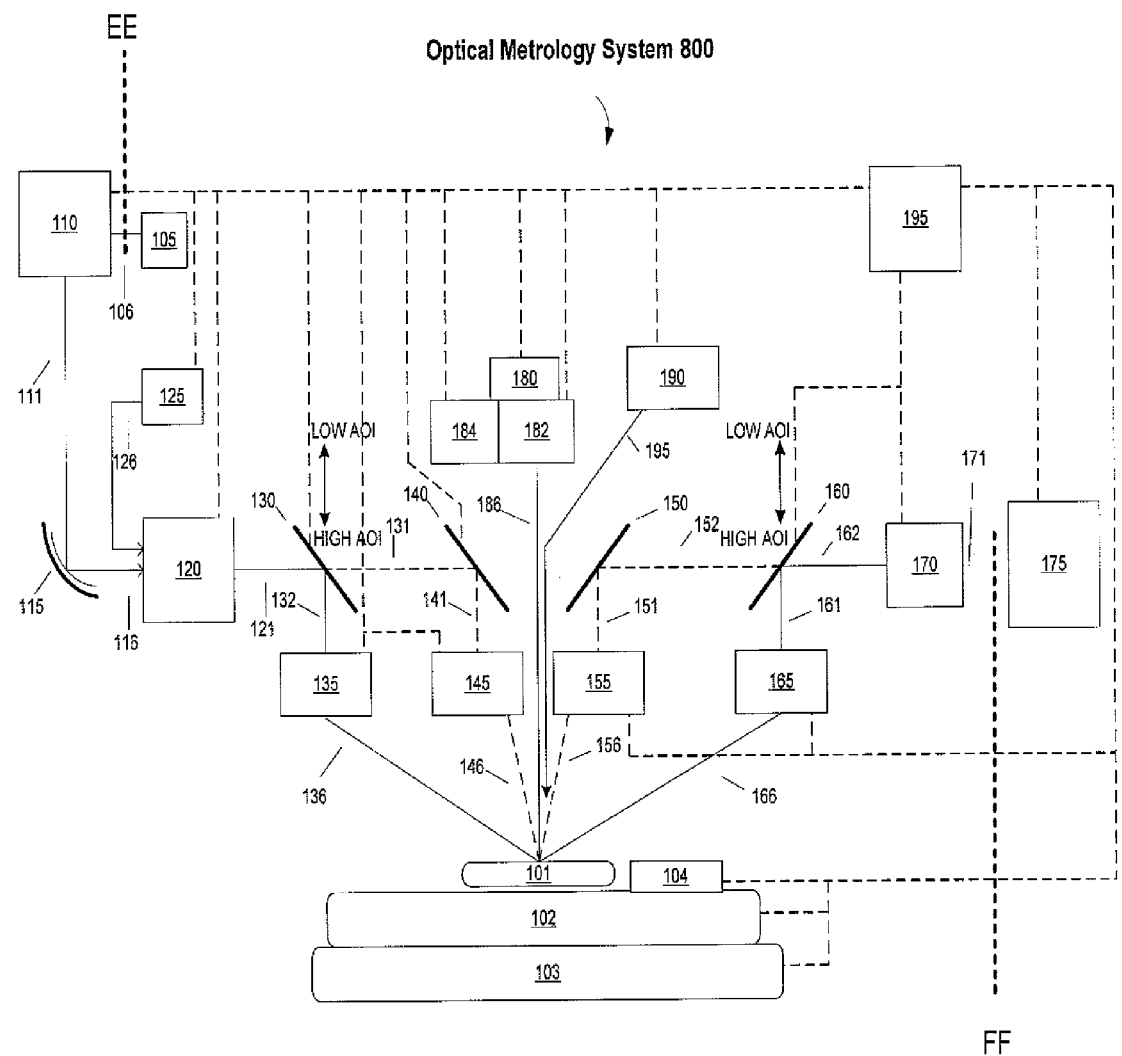
FIG. 8 is an exemplary diagram of an optical metrology system depicting points of measurements of the signal.

FIG. 8 is an exemplary diagram of an optical metrology system 800 depicting points of measurements of the signal. Optical metrology system 800 depicts a similar set of optical subsystems as those depicted in FIG. 1B. In addition, position EE in the optical path in FIG. 8 represents a point where measurements with photodetectors (not shown) may be made in the illumination side which can be the same position as positions AA and BB in FIG. 6. Similarly, position FF in the optical path in FIG. 8 represents a point where measurements with photodetectors (not shown) may be made in the detection side which can be the same position as positions CC and DD in FIGS. 7A and 7B respectively. Measurements at specific points along the optical path provide signal data for use in comparing against the set values of the one or more signal criteria. For example, the one or more signal criteria may include a signal intensity of 100 joules at point EE and at least 2 joules at point FF in FIG. 8. In another embodiment, the one or more signal criteria can include a signal intensity of 120 joules at point EE and at least 2 joules at point FF and a signal of 120 joules signal intensity to 0.10 joules noise or SNR of 1,200 at point EE in FIG. 8. As mentioned above, the one or more signal criteria may be set at various points along the optical path or on specific optical components along the optical path such as the light source subsystem depicted in FIG. 6 or the detector subsystem depicted in FIGS. 7A and 7B.

Although exemplary embodiments have been described, various modifications can be made without departing from the spirit and/or scope of the present invention. For example, although light intensity was primarily used to describe the embodiments of the invention, light intensity, phase change, and other signal characteristics may also be used. Furthermore, the elements required for the design of the optical metrology system are substantially the same whether the optical metrology system is integrated in a fabrication cluster or used in a standalone metrology setup. Therefore, the present invention should not be construed as being limited to the specific forms shown in the drawings and described above.

What is claimed:

1. An apparatus for designing an optical metrology system, the optical metrology system measuring structures on a workpiece, the optical metrology system configured to meet one or more signal criteria, the apparatus comprising:

an optical metrology signal model for an optical metrology system, the optical metrology system designed to measure structures on a workpiece and having an optical path including optical components, the optical metrology signal model configured based on an initial design of the optical metrology system, the initial design based on a range of determined capabilities of the optical metrology system, and configured to store for each optical component in the optical path a corresponding function that determines output signal characteristics based on input signal characteristics;

an operating data collector configured to collect signal data from input sources and associate the collected signal data to a criterion of the one or more signal criteria; and a model analyzer configured to develop and store an initial design of the optical metrology system, compare calculated one or more signal criteria using the collected signal data with one or more signal criteria set from input sources, and if the calculated one or more signal criteria do not match the set one or more signal criteria, to determine and implement design modifications of the optical metrology system, and iterate an operation for updating the optical metrology signal model with the design modifications, collecting signal data with the operating data collector, and performing the comparison of collected signal data to the set one or more signal criteria until the calculated one or more signal criteria match the set one or more signal criteria.

2. The apparatus of claim 1 wherein the workpiece is a wafer in a semiconductor application.

3. The apparatus of claim 1 wherein the one or more signal criteria include signal intensity and/or signal to noise ratio.

4. The apparatus for claim 3 wherein the range of capabilities of the optical metrology system comprises measurement of line and space repeating structures, two dimensional repeating structures, and complex repeating structures comprising posts, contact holes, vias, islands, and concave or convex three dimensional structures, or combinations of two or more thereof.

5. The apparatus of claim 3 wherein developing the metrology signal model comprises developing a function for each optical component in the optical path that includes an input signal intensity and a corresponding output signal intensity determined based on the input signal intensity and type and specification of the optical component.

6. The apparatus of claim 3 wherein the optical components comprises:
light sources, a homogenizer for the light sources, illumination focusing optics, a polarizer on the illumination side, a polarizer on the detection side, focusing optics on the detection side, detector gratings, spectrometers, a nitrogen-purging system, flip-in mirrors or lenses or collimating mirrors.

7. The apparatus of claim 1 wherein the one or more signal criteria comprise a signal-to-noise ratio (SNR) criterion and/or repeatability of measurement criterion.

8. The apparatus of claim 1 wherein the one or more signal criteria comprise a signal intensity criterion or a signal-to-noise ratio (SNR) criterion or repeatability of measurement criterion or any combination of two or more thereof.

9. The apparatus of claim 8 wherein the signal intensity criterion set for optical components comprising illumination focusing optics comprises an efficiency of conversion of input signal intensity to output signal intensity of 80% or better.

10. The apparatus of claim 8 wherein the signal intensity criterion includes a minimum signal intensity input into the spectrometer of 2 joules, an SNR criterion includes a target of 2000 to 1, and a repeatability of measurement criterion equal to or less than a 3-sigma of 4 nanometers or less.

11. The apparatus of claim 3 wherein collecting of signal data includes using data measured in a breadboard prototype of the optical metrology system or using data from vendors of the optical components.

12. The apparatus of claim 3 wherein modifying the design of the optical metrology system includes using two or more light sources utilizing different ranges of wavelengths.

13. The apparatus of claim 3 wherein modifying the design of the optical metrology apparatus includes using a separate detector for each of the two or more diffraction signals.

14. The apparatus of claim 3 wherein modifying the design of the optical metrology system includes selecting a first polarizer in the illumination path and a second polarizer in the detection path, wherein the first and second polarizers are configured to increase the signal to noise ratio of the illumination and detection beams respectively.

15. The apparatus of claim 3 wherein modifying the design of the optical metrology system includes replacing focusing optics with different quality coatings.

16. The apparatus of claim 3 wherein modifying the design of the optical metrology system includes using a selectable angle of incidence for the one or more illumination beam to optimize accuracy of the diffraction measurement instead of a fixed angle of incidence for the illumination beams.

17. The apparatus of claim 3 wherein modifying the design of the optical metrology system includes using higher efficiency grating and/or higher efficiency signal detector.

18. The apparatus of claim 3 wherein modifying the design of the optical metrology system includes using an environment purged with nitrogen gas.

19. The apparatus of claim 3 further comprising:
an optical metrology system constructed to meet the one or more signal criteria and configured to measure a structure in a workpiece, the measurement generating a diffraction signal; and
a processor configured to extract at least one profile parameter of the structure from the measured diffraction signal using profile extraction systems that include a regression method, a library method, or a machine learning systems method.

20. The apparatus for claim 1 wherein the workpiece is a wafer in a semiconductor application and wherein the optical metrology system is integrated in a fabrication cluster or the optical metrology system is part of a standalone metrology device.

* * * * *